US00PP27155P2

(12) United States Plant Patent
Deng et al.

(10) Patent No.: US PP27,155 P2
(45) Date of Patent: Sep. 13, 2016

(54) ***CALADIUM* PLANT NAMED 'HEARTS DESIRE'**

(50) Latin Name: *Caladium×hortulanum*
Varietal Denomination: Hearts Desire

(71) Applicant: Florida Foundation Seed Producers, Inc., Marianna, FL (US)

(72) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/998,921

(22) Filed: Mar. 4, 2016

(51) Int. Cl.
*A01H 5/12* (2006.01)

(52) U.S. Cl.
USPC ..... Plt./373

(58) Field of Classification Search
USPC ..... Plt./263.1, 373
See application file for complete search history.

*Primary Examiner* — Susan McCormick Ewoldt
*Assistant Examiner* — Karen Redden
(74) *Attorney, Agent, or Firm* — Christopher & Weisberg, P.A.

(57) ABSTRACT

A new and distinct cultivar of *Caladium* plant named 'Hearts Desire', characterized by its mounding growth habit, heart-shaped green leaves that have a white center, white mid and primary veins, numerous red purple spots and speckles along the netted veins, and plants that are attractive in containers and sunny or shady landscapes.

4 Drawing Sheets

ACKNOWLEDGMENT OF FEDERAL RESEARCH SUPPORT

This invention was made with government support under FLA-BRA-04162 awarded by the Cooperative State Research, Education, and Extension Service, USDA and under FLA-GCR-005065 awarded by the National Institute of Food and Agriculture, USDA. The government has certain rights in the invention.

Genus and species: *Caladium×hortulanum.*

Cultivar denomination: 'Hearts Desire'.

CROSS-REFERENCE TO RELATED APPLICATION n/a

BACKGROUND OF THE NEW CULTIVAR

The present invention relates to a new and distinct cultivar of *caladium* plant, botanically known as *Caladium×hortulanum*, commercially referred to as a fancy leaf-type *caladium* and hereinafter referred to by the name 'Hearts Desire'.

*Caladiums* (also referred to as *Caladium* plants) are ornamental aroids frequently used as pot and landscape plants for their colorful foliage and ease of growing. The objective of the Inventors' breeding program is to create new *Caladium* cultivars that have numerous leaves, attractive foliage, and exceptional container and landscape performance.

The new *Caladium* cultivar 'Hearts Desire' originated from a cross between 'Grey Ghost' (commercial cultivar, not patented) and 'Miss Muffet' (commercial cultivar, not patented) that was made in Bradenton, Fla., in summer 2003. The new *Caladium* cultivar 'Hearts Desire' was discovered and selected by the inventors as a single plant in Bradenton, Fla. in 2004. The *Caladium* cultivar 'Hearts Desire' has been found to retain its distinctive characteristics through at least nine generations of successive asexual propagations via tuber divisions since 2004.

Plant Breeder's Rights for this cultivar have not been applied for. 'Hearts Desire' has not been made publicly available more than one year prior to the filing of this application.

SUMMARY OF THE INVENTION

The new *Caladium* cultivar has not been observed under all possible environmental conditions. The phenotype may vary somewhat with variations in environment such as temperature, light intensity, water status, fertilizer rate and type, without, however, any variance in genotype.

The following are the most outstanding and distinguishing characteristics of this new *Caladium* cultivar when grown under (normal or standard) horticultural practices in Wimauma, Fla. The combination of these characteristics distinguishes 'Hearts Desire' as a new and distinct cultivar of *Caladium:*

1. Symmetrical, rounded plant form.
2. Mounding, dense and bushy growth habit.
3. Heart-shaped leaves that have green margins and a white center with multiple white mid and primary veins, numerous red purple spots of various sizes and shapes, and red purple speckles throughout the leaf surface.
4. Attractive plants in containers or sunny or shady landscapes.

Plants of the new cultivar 'Hearts Desire' differ from its female parent 'Grey Ghost' in the following characteristic:

1. Leaves of the new cultivar have a green center and red purple spots and speckles, whereas leaves of 'Grey Ghost' have a white center and no spots or blotches.

The new *Caladium* cultivar 'Hearts Desire' differs from its male parent 'Miss Muffet' in the following characteristics:

1. Plants of the new cultivar 'Hearts Desire' are much taller and wider than plants of 'Miss Muffet'.

2. Leaves of the new cultivar 'Hearts Desire' are darker green, larger and wider, and its spots and speckles are red purple, whereas leaves of 'Miss Muffet' have a more lime green coloring and the spots are dark burgundy.
3. The petioles of 'Hearts Desire' are longer, more arching, and green colored, whereas the petioles of 'Miss Muffet' are shorter and have a pinkish brown coloring.

The new *Caladium* cultivar 'Hearts Desire' can be compared to the *Caladium* cultivar 'Galaxy' (not patented). In side-by-side comparisons conducted in Wimauma, Fla., plants of the new *Caladium* cultivar differed from plants of 'Galaxy' *caladium* in the following characteristics:

1. Plants of 'Hearts Desire' were taller and more open than plants of 'Galaxy' *caladium.*
2. Leaves of 'Hearts Desire' have a lighter green coloring, whereas leaves of 'Galaxy' *caladium* have a darker green color.
3. Leaves of 'Hearts Desire' have red purple spots of various sizes and shapes, whereas leaves of 'Galaxy' have the white to pinkish spots.

DESCRIPTION OF THE FIGURES

The accompanying photographs (as shown in FIGS. 1-4) illustrate the overall appearance of the new *Caladium* cultivar.

These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION OF THE CULTIVAR

Figure 1:
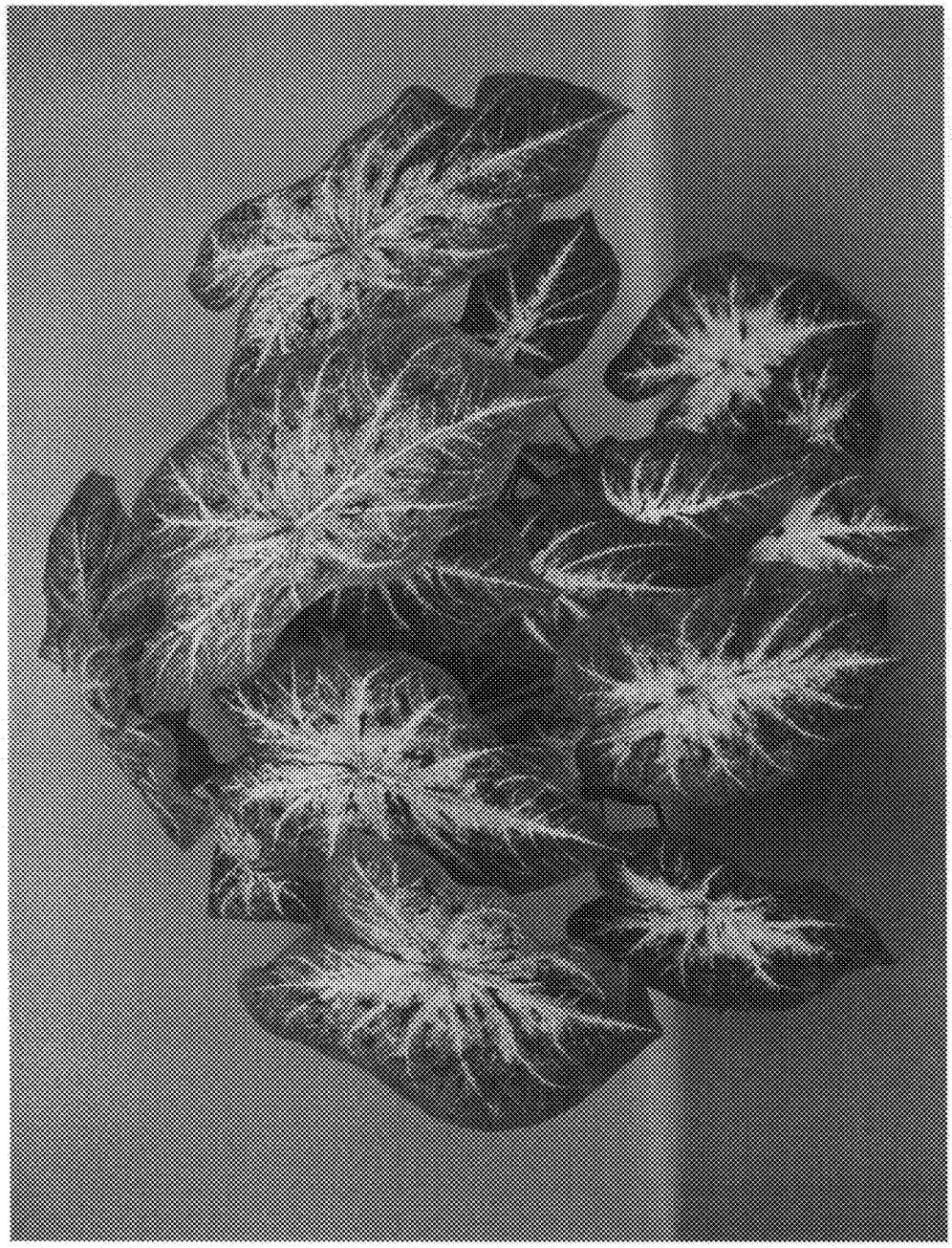
FIG. 1 shows a photograph of a side view of a typical plant of the new *Caladium* cultivar 'Hearts Desire' grown in a 20-cm diameter container in a shadehouse.
Figure 2:
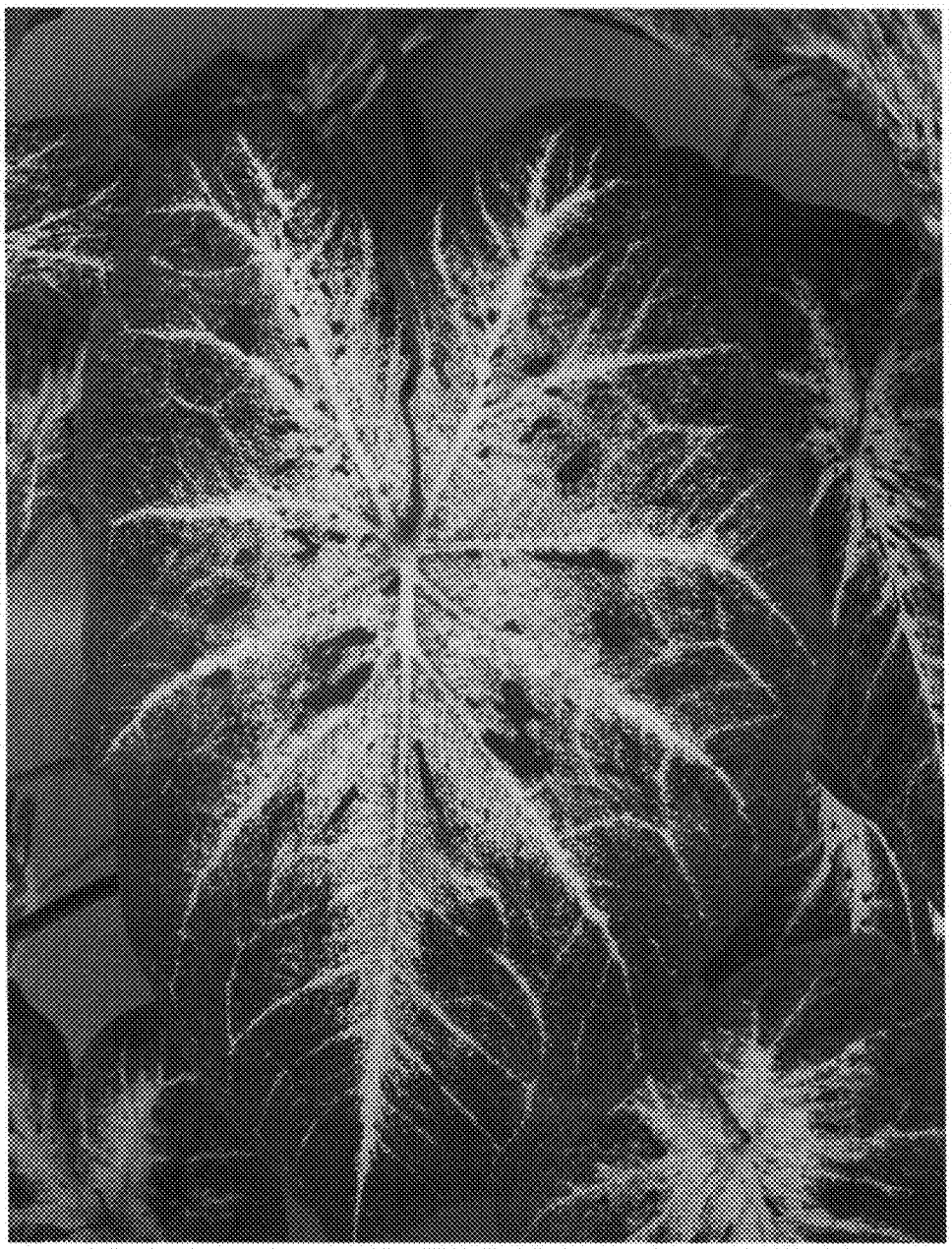
FIG. 2 shows a photograph of a top view of a typical leaf of the new *Caladium* cultivar 'Hearts Desire' grown in a 20-cm diameter container in a shadehouse.
Figure 3:
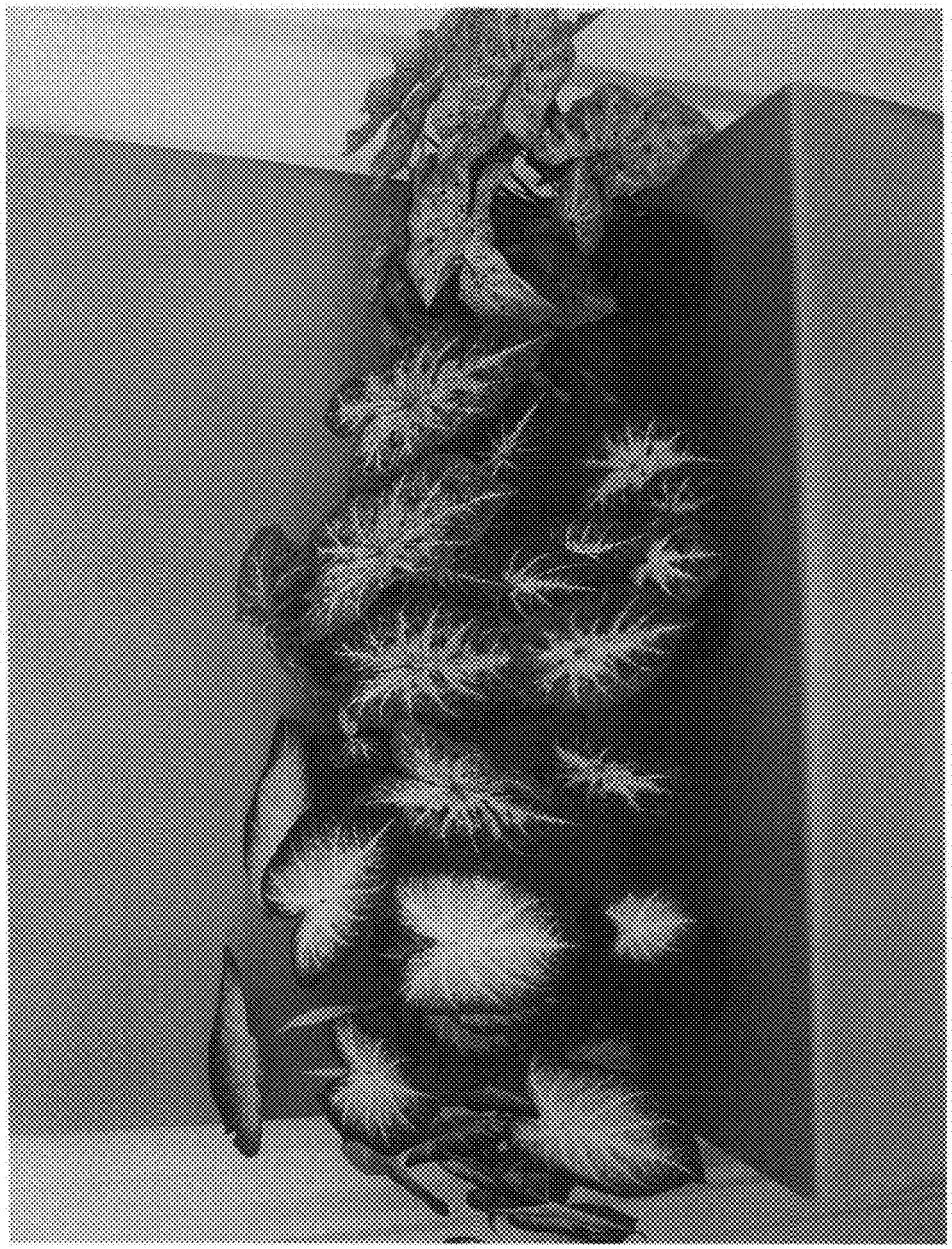
FIG. 3 shows a photograph of a side view of typical plants of 'Hearts Desire' (center), 'Aaron' (left; a cultivar almost identical to 'Grey Ghost' in plant form, growth habit, leaf shape and color), and 'Miss Muffet' (male parent) (right) grown in 20-cm diameter container in a shadehouse.
Figure 4:
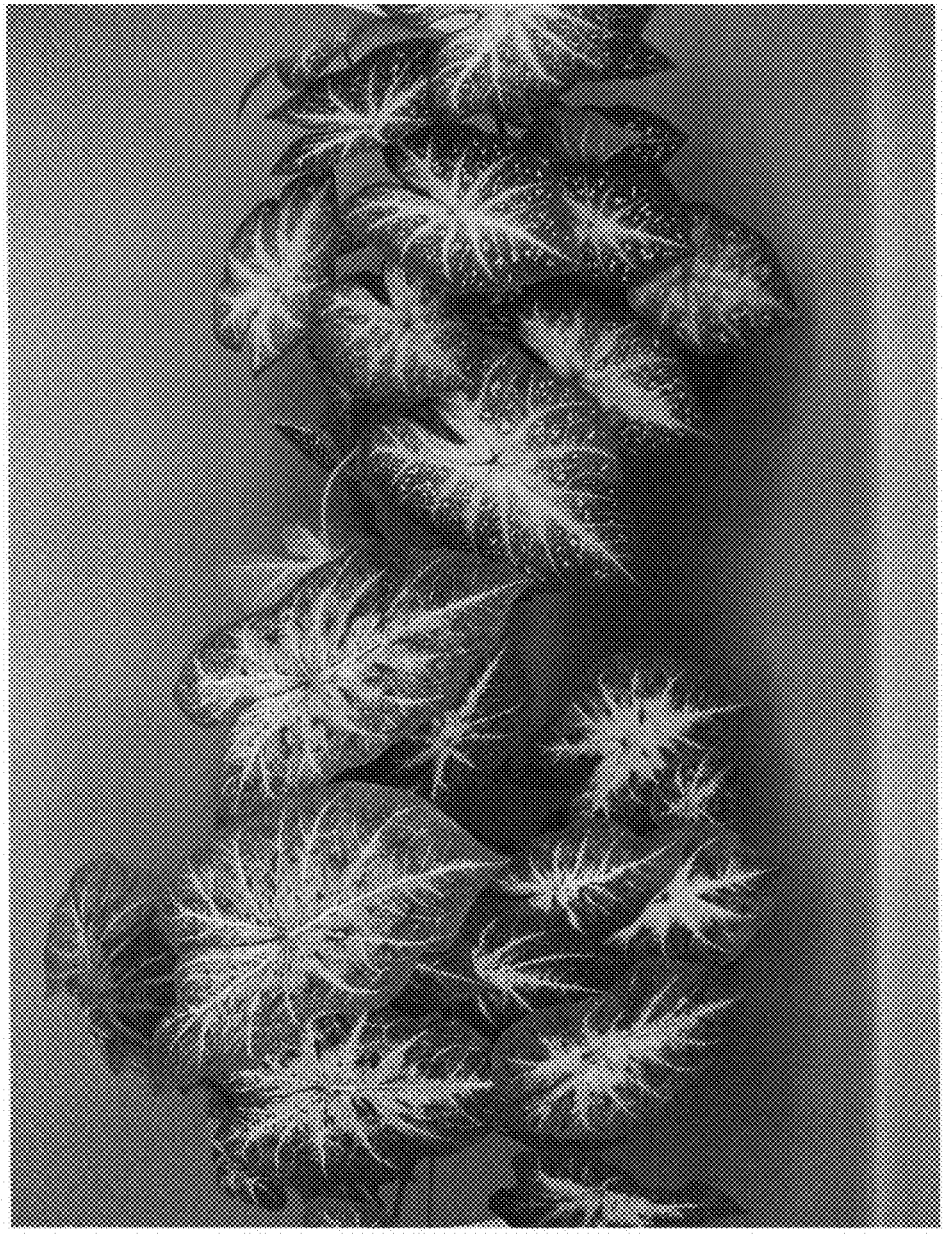
FIG. 4 shows a photograph of a side view of typical plants of 'Hearts Desire' (left) and 'Galaxy' (right) grown in 20-cm diameter container in a shadehouse.

In the following description, color references are made to The Royal Horticultural Society (R.H.S.) Colour Chart, 1986 Edition, except where general terms of ordinary dictionary significance are used. The features of 'Hearts Desire' described herein are shown in FIGS. 1-4.

Description of Growing Conditions

The following observations and measurements describe plants grown in 20-cm containers in Wimauma, Fla., during the summer in a polypropylene-covered shadehouse. All plants were grown under conditions and practices similar to those generally used in commercial *Caladium* production.

During the production of the plants, day temperatures ranged from approximately 75° F. to 92° F., night temperatures ranged from approximately 66° F. to 76.1° F. The shadehouse was covered with shadecloth that excluded approximately 30% natural light. Plants grown in the shadehouse were approximately seven weeks from planting tubers when the photographs and the detailed description were taken.

Botanical Description

Botanical classification:
- *Family.*—Araceae.
- *Botanical name.*—*Caladium×hortulanum.*
- *Common name.*—*Caladium.*
- *Cultivar.*—'Hearts Desire' (*Caladium×hortulanum* cultivar 'Hearts Desire').

Parentage:
- *Female or seed parent.*—'Grey Ghost'.
- *Male or pollen parent.*—'Miss Muffet'.

Propagation:
- *Type.*—By tubers and by tuber divisions.
- *Time to initiate roots, summer.*—Approximately seven to ten days at 32° C.
- *Time to initiate roots, winter.*—Approximately two to three weeks at 24° C.

Tuber description: Jumbo-sized (6.4 to 8.9 cm in diameter) tubers are multi-segmented, bearing six to nine dominant buds.
- *Height of tubers.*—3.0 to 3.6 cm.
- *Diameter of tubers.*—6.0 to 8.5 cm.
- *Texture.*—Thick, starchy inside; slightly brittle between tuber segments.
- *Color.*—Epidermis, Close to brown (RHS 200D); but lighter. Interior, yellow (RHS 13A).
- *Root description.*—Dense, thick and white fleshy roots white (RHS 155D).

Plant description:
- *Type.*—Herbaceous perennial.
- *Plant form.*—Upright, outwardly arching and symmetrical plant.
- *Growth habit.*—Leaf petioles arising from tubers; petioles mostly upright and curving outwardly with development. Dense foliage, suitable for containers with 10.0 cm or larger diameters.
- *Plant height, from soil level to top of leaf plane, shadehouse-grown plants.*—Approximately 52 cm.
- *Plant height, from soil level to top of inflorescences, shadehouse-grown plants.*—Approximately 33 cm.
- *Plant spread, shadehouse-grown plants.*—Approximately 74 cm×79 cm.

Foliage description (shadehouse-grown):
- *Length, shadehouse-grown plants.*—Approximately 31.0 cm.
- *Width, shadehouse-grown plants (flattened).*—Approximately 20.5 cm.
- *Shape.*—Ovate.
- *Apex.*—Acuminate to acute.
- *Base.*—Cordate.
- *Margin.*—Entire.
- *Texture, upper surface.*—Smooth, glabrous.
- *Texture, lower surface.*—Smooth, glabrous; glaucous.
- *Venation pattern.*—Palmate-pinnate.

Leaf color, shadehouse-grown plants:
- *Fully expanded leaves.*—Upper surface: Center: Close to white (RHS 155D), with numerous red-purple (RHS 60A) spots of variable sizes and shapes and speckling of red-purple (RHS 60D) and green (RHS 143A to 143B) along the veins. Border and margins: Close to green (RHS 143A to 143B). Basal notch: Close to red-purple (RHS 60B), with a thin line of red-purple (RHS 60B) running from the basal notch to sinus cavity. Venation: Midrib: Close to white (RHS 155D). Primary: Close to white (RHS 155D), with a thin line of green (RHS 143A and 143C) running down the center of the vein. Lower surface: Center: Close to greyed-green (RHS 191B), with spots of greyed-purple (RHS 187D) and white (RHS 155D) and dotting of greyed-red (RHS 182D) along the veins. Border and margins: Close to greyed-green (RHS 191C). Venation: Midrib: Close to white (RHS 155A). Primary veins: Close to yellow-green (RHS 145A to 145D).

Petiole:

*Aspect*.—Mostly erect, curving outwardly with development.

*Length, shadehouse-grown plants*.—Approximately 33 to 45 cm.

*Diameter, distal, shadehouse-grown plants*.—Approximately 6.3 mm.

*Diameter, proximal, shadehouse-grown plants*.—Approximately 9.8 mm.

*Strength*.—Strong, flexible.

*Color, shadehouse-grown plants*.—Close to yellow-green (RHS 144A) or yellow-white (RHS 158C) with specs of yellow-green (RHS 144D).

*Wing length, shadehouse-grown plants*.—Approximately 8.0 cm to 13 cm.

*Wing diameter, shadehouse-grown plants*.—Approximately 8.3 mm to 13.2 mm.

*Wing color, shadehouse-grown plants*.—Close to yellow-green (RHS 144A) with streaks of yellow-green (RHS 144D).

Inflorescence description: Plants of 'Hearts Desire' produce inflorescences only occasionally.

*Inflorescence arrangement*.—Upright hooded spathes surrounding a columnar spadix borne on an upright scape. The spadix carries sessile, female and male flowers separated into two zones. Female flowers arranged on the lower one-third of the spadix; male flowers arranged on the upper two-thirds of the spadix. Sterile flowers develop between female and male flower zones. Spadix constricts near the sterile flower zone.

*Fragrance*.—None detected.

*Natural flowering season/longevity*.—Plants of 'Hearts Desire' typically flower during spring or early summer in central Florida. Flowers develop about seven weeks after growth commence. Inflorescences last about four days before fading.

*Spathe*.—Length: Approximately 14.5 cm. Width: Distal: Approximately 3.5 cm. Proximal: Approximately 2.6 cm. Shape: Ovate to somewhat obovate. Apex: Acute to acuminate. Base: Tapering. Margin: Entire. Texture: Upper and lower surfaces: Smooth, glabrous. Color: Front surface: Upper two-thirds: Close to green-white (RHS 157B) with streaking of green-white (RHS 157A). Lower one-third: Close to yellow-green (RHS 144A) or yellow-green (RHS 145B) with streaks of yellow-green (RHS 144B). Rear surface: Upper two-thirds: Close to yellow-green (RHS 145A.). Lower one-third: Close yellow-green (RHS 145B) with streaks of yellow-green (RHS 144B).

*Spadix*.—Length, entire spadix: Approximately 6.5 cm. Length, male flower zone: Approximately 3.9 cm. Length, sterile flower zone: Approximately 1.1 cm. Length, female flower zone: Approximately 1.3 cm. Diameter, male flower zone: Approximately 8 mm. Diameter, sterile flower zone: Approximately 6 mm. Diameter, female flower zone: Approximately 9.5 mm. Shape: Spindle-shaped to columnar. Apex: Obtuse. Base: Obtuse. Aspect: Upright. Color, mature, male zone: Close to greyed-yellow (RHS 160B). Color, mature, sterile zone: Close to yellow-white (RHS 158D). Color, mature, female zone: Close to yellow-white (RHS 158C). Male flowers: Quantity per spadix: Approximately 215. Shape: Obovate. Height: Approximately 2.3 mm. Diameter: Approximately 2.3 mm. Amount of pollen: Scant. Female flowers: Quantity per spadix: Approximately 160. Shape: Obovate. Height: Approximately 1 mm. Diameter: Approximately 1 mm.

*Scape*.—Length: Approximately 22.6 cm. Diameter: Approximately 6 mm. Strength: Sturdy, flexible. Aspect: Erect, upright, but with some arching. Texture: Smooth, glabrous, glaucous. Color, proximal: Close to yellow-green (RHS 145C) with streaks of yellow-green (RHS 144A) or yellow-green (RHS 146C) with streaking of yellow-green (RHS 146A). Just below spathe: Close to green (RHS 144A and 144B).

*Seed and fruit*.—Seed and fruit development has not been observed on inflorescences that were not hand-pollinated.

Disease/pest resistance: None.

Temperature tolerance: Tolerant to temperatures ranging from approximately 7° C. to approximately 40° C.

Sunburn tolerance: Moderate to high levels of tolerance to sunburns.

Comparison with Known Cultivars

The new cultivar 'Hearts Desire' was evaluated for tuber production in Wimauma, Fla. in 2009 and 2014. The soil was EauGallie fine sand with about 1% organic matter and a pH value between 6.2 and 7.4. *Caladium* plants were grown in the field using a plastic-mulched raised-bed system. For the 2009 evaluation, beds were fumigated on 27 February with a mixture of 50% methyl bromide and 50% chloropicrin (by volume) at the rate of 196 $kg \cdot ha^{-1}$. *Caladium* seed pieces were planted on 9 Apr. 2009 at approximately 15-cm spacing between rows and in rows. Drip tapes were buried under the plastic mulch and delivered approximately 6 mm of water to the bed per day. Fertigation began when young *caladium* plants emerged from the soil, supplying soluble fertilizer (6N-0.8P-3.9K) at the rate of about 1.9 kg of $nitrogen \cdot ha^{-1} \cdot day^{-1}$ and a total 290 kg of $nitrogen \cdot ha^{-1}$ per growing season. One teaspoon (approximately seven grams) of OSMOCOTE® controlled-release fertilizer (15N-2.6P-10K, 5-6 months) was applied to each plant on 21 July. Tubers were dug from 30 November to 2 Dec. 2009. Tuber grading was by the maximum diameter: Super Mammoth (greater than 11.4 cm), Mammoth (8.9 to 11.4 cm), Jumbo (6.4 to 8.9 cm), No.1 (3.8 to 6.4 cm), and No. 2 (2.5 to 3.8 cm). Tuber grades and counts were converted into a production index to show the relative economic value of the harvested tubers per field plot: PI=8n (Supper Mammoth)+6n (Mammoth)+4n (Jumbo)+2n (No.1)+1n (No.2), where n=number of tubers in the grade.

For the 2014 evaluation, beds were fumigated on 9 January with PIC-CLOR 60™ liquid fumigant (39.0% 1,3-dichloropropene and 59.6% chloropicrin) at 448 $kg \cdot ha^{-1}$. PLANTA- COTE® Pluss, a controlled-release fertilizer (14N-3.9P-12.5K, 12 months, X-Calibur Plant Health Company LLC, Summerville, S.C.), was incorporated into the bed at 336 $kg \cdot ha^{-1}$. *Caladium* seed pieces were planted on 16 and 28 April at approximately 15-cm spacing between rows and in rows. Irrigation was by seepage. *Caladium* plants were fertilized with 600 ppm of nitrogen with a commercial water-soluble fertilizer (20N-8.7P-16.6K, Southern Agricultural Insecticides, Inc., Palmetto, Fla.) on 18 September and 1 Oct. 2014. Tubers were dug from 1 December to 9 Dec. 2014, followed by the same washing, drying, weighing, grading, and counting procedures as were done in 2009.

Field plots were arranged each season in three randomized complete blocks, and each plot (1.2 $m^2$) was planted with 30 *caladium* seed pieces. One commercial cultivars 'Miss Muffet' was included as a control in each block. Analyses of variance were conducted using the PROC GLM procedure in SAS (SAS Institute, Cary, N.C.) to compare the tuber yields of 'Hearts Desire' to that of 'Miss Muffet'.

Table 1 shows the tuber weight, marketable tubers, production index, and grade distribution of the new cultivar 'Hearts Desire' grown in Wimauma, Fla. in 2009 and 2014, as compared to those of 'Miss Muffet'. Values presented for each year are means of three plots in three randomized complete blocks.

TABLE 1

| Cultivars | Tuber Weight (kg) | Tuber Marketable (no.) | Tuber Production index[z] | Tuber grade distribution (%) Super Mammoth |
|---|---|---|---|---|
| | Year 2009 | | | |
| Hearts Desire | 4.3 ns | 39.7 ns | 117.0 ns | 2.5 ns |
| Miss Muffet | 2.5 ns | 28.0 ns | 72.7 ns | 0 ns |
| | Year 2014 | | | |
| Hearts Desire | 2.6 ns | 33.7 ns | 87.0 ns | |
| Miss Muffet | 3.3 ns | 33.7 ns | 94.7 ns | |

| Cultivars | Tuber grade distribution (%) Mammoth | Jumbo | No. 1 | No. 2 |
|---|---|---|---|---|
| | Year 2009 | | | |
| Hearts Desire | 14.6 ns | 24.5 ns | 33.3 b[y] | 25.1 ns |
| Miss Muffet | 8.2 ns | 23.4 ns | 49.9 a | 18.6 ns |
| | Year 2014 | | | |
| Hearts Desire | 2.0 ns | 32.0 ns | 52.4 ns | 13.6 ns |
| Miss Muffet | 2.8 ns | 43.6 ns | 38.6 ns | 15.1 ns |

[z]The production index is an indicator of economic value of the crop harvested and is calculated as: N (No.2s) + 2N (No. 1s) + 4N (Jumbos) + 6N (Mammoth) + 8N (Super Mammoth); where N = number of tubers in each grade. Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm).
[y]Mean values with the same letters within columns are not significantly different at $P \leq 0.05$.
ns: not significantly different at $P < 0.05$.

As shown in Table 1, there were no significant differences between the new cultivar 'Hearts Desire' and the control cultivar 'Miss Muffet' in tuber weights (4.3 and 2.5 kg in 2009, and 2.6 and 3.3 kg in 2014), the number of marketable tubers (39.7 and 28.0 in 2009, and 33.7 and 33.7 in 2014), and production index (117.0 and 72.7 in 2009, and 87.0 and 94.7 in 2014) in both growing seasons. Overall, 'Hearts Desire' and 'Miss Muffet' showed similar tuber size distributions, except that 'Hearts Desire' produced fewer No.1-grade tubers in 2009.

Table 2 shows a comparison of the plant height, number of leaves, leaf length, and leaf width of the new cultivar 'Hearts Desire' with 'Miss Muffet', approximately 4 months after planting 2.54-cm tuber pieces (propagules) in ground beds in full sun in 2009 and 2014. Values presented are means of data from three replications and three plants measured per plot per year over two years.

TABLE 2

| Cultivars | Plant height (cm) | Leaves (no.) | Leaf length[z] (cm) | Leaf width[y] (cm) |
|---|---|---|---|---|
| Hearts Desire | 46.1 a[x] | 19.3 ns | 25.5 a | 15.7 a |
| Miss Muffet | 25.0 b | 19.7 ns | 20.2 b | 11.9 b |

[z]Leaf length was measured on the largest leaves along the longest line from the leaf lobe to the leaf tip.
[y]Leaf width was measured on the largest leaves across the widest middle part.
[x]Mean values with the same letters within columns are not significantly different at $P \leq 0.05$.
ns: not significantly different at $P \leq 0.05$.

As shown in Table 2, the new cultivar 'Hearts Desire' is relatively tall, with an average plant height of 46.1 cm, 84% greater than the height of 'Miss Muffet', which is known for its dwarf stature. Plants of 'Hearts Desire' had similar numbers of leaves as plants of 'Miss Muffet', but leaves of 'Hearts Desire' were 5.3 cm longer and 3.8 cm wider than leaves of 'Miss Muffet'.

Table 3 shows the landscape performance of the new cultivar 'Hearts Desire' with 'Miss Muffet' when planted in ground beds in full sun in 2009 and 2014. Values presented are means of three replications in each year.

Landscape performance was evaluated on the same plots used for evaluating tuber production. A scale of 1 to 5 was used with 1 being very poor (few leaves and lack of vigor), and 5 being excellent (full plants, numerous leaves, and bright color display). Leaf sun tolerance was evaluated on a scale of 1 to 5, with 1 being very susceptible to sunburn (leaves having numerous sun-damaged areas or holes) and 5 being resistant to sunburn (no visible sun-damaged areas). Three to four evaluations were conducted in each growing season for plant performance and sunburn tolerance. Evaluations were done in August, September and October 2009, and July, August, September, and October in 2014.

TABLE 3

| Cultivars | 2009 August | 2009 September | 2009 October | 2014 July | 2014 August | 2014 September | 2014 October |
|---|---|---|---|---|---|---|---|
| Hearts Desire | 4.8 a | 3.8 ns | 4.0 ns | 4.4 ns | 4.4 ns | 3.7 ns | 4.0 a |
| Miss Muffet | 3.7 b | 3.8 ns | 3.8 ns | 3.4 ns | 4.4 ns | 4.0 ns | 3.4 b |

Plants were rated on a scale of 1 to 5, with 1 being very poor, 3 fair and acceptable, and 5 being excellent in plant vigor, fullness, and color display, In August, September and October 2009, and in July, August, September, and October 2014. Mean values with the same letters within columns are not significantly different at $P \leq 0.05$.
ns: Not significantly different at $P < 0.05$.

As shown in Table 3, plants of the new cultivar 'Hearts Desire' received good to excellent performance ratings (3.7 to 4.8) in both 2009 and 2014 growing seasons, better than or comparable to the performance ratings of 'Miss Muffet' (3.4 to 4.4) in all three evaluations in 2009 and all four evaluations in 2014.

Table 4 shows the leaf sunburn tolerance of the new cultivar 'Hearts Desire' with 'Miss Muffet' when tuber pieces were planted in ground beds and plants were grown in full sun in 2009 and 2014. Values presented are means of three replications in each year.

Leaf sun burn tolerance was evaluated on a scale of 1 to 5, with 1 being very susceptible to sun burns (leaves having numerous sun-damaged areas or holes) and 5 being resistant to sunburn (no visible sun-damaged areas). A total of seven evaluations were conducted for plant performance over two growing seasons in August, September, and October 2009, and in July, August, September and October 2014.

TABLE 4

| | 2009 | | | 2014 | | | |
|---|---|---|---|---|---|---|---|
| Cultivar | August | September | October | July | August | September | October |
| Hearts Desire | 4.0 ns | 3.5 ns | 3.8 ns | 4.6 ns | 4.0 ns | 3.0 b | 4.0 ns |
| Miss Muffet | 4.8 ns | 4.5 ns | 4.2 ns | 4.2 ns | 4.5 ns | 4.1 a | 4.1 ns |

Plant sunburn tolerance was rated on a scale of 1 to 5, with 1 being very poor, 3 fair and acceptable, and 5 being excellent without showing any signs of leaf burns or holes caused by sunburn on leaf surfaces, in August, September and October 2009, and in July, August, September and October 2014. Mean values with the same letters within columns are not significantly different at P≤0.05. ns: Not significantly different at P≤0.05.

As shown in Table 4, plants of the new cultivar 'Hearts Desire' showed acceptable sunburn tolerance in both 2009 and 2014 growing seasons, with sunburn tolerance ratings between 3.0 to 4.6 in seven evaluations. The sunburn tolerance rating of the new cultivar 'Hearts Desire' was significantly lower than that of 'Miss Muffet' in October 2014.

The suitability of the new cultivar 'Hearts Desire' for pot plant production was evaluated by forcing tubers in 11.4-cm containers in spring 2008. Intact No. 1-sized tubers (>3.8 cm and <6.4 cm in diameter) were planted in a peat/vermiculite mix (VERGRO™ Container Mix A, Verlite, Tampa, Fla.) on 17 Apr. 2008. The study was conducted in a greenhouse with 45% light exclusion. Average daily temperatures in the greenhouse ranged from a low of 16° C. at night to 29° C. during the day during the experiment. Potted plants were arranged on metal benches in the greenhouse in a randomized complete block design with eight replications. Plant height, plant width, number of leaves, and foliar characteristics were recorded on 12 Jun. 2008, 8 weeks after planting. Quality of the potted *Caladium* plants was rated on a scale of 1 to 5, 1=very poor, few leaves, totally unacceptable as potted plants, and 5=very attractive, with many bright, colorful leaves, a full plant, a symmetrical shape, and an appropriate height.

Table 5 shows a comparison of number of days to sprout, plant height, plant width, leaf number, leaf length, leaf width, and quality rating of 'Hearts Desire' with 'Miss Muffet' when intact and de-eyed tubers were forced in containers in spring 2008.

TABLE 5

| | Days to sprout[z] | | Plant height (cm) | |
|---|---|---|---|---|
| Cultivars | Intact | De-eye | Intact | De-eye |
| Hearts Desire | 16 b | 24 ns | 39.6 a | 39.5 a |
| Miss Muffet | 18 a | 24 ns | 26.3 b | 26.2 b |
| | **Leaves (no.)** | | **Leaf length (cm)** | |
| Cultivars | Intact | De-eye | Intact | De-eye |
| Hearts Desire | 11.0 ns | 30.2 ns | 30.1 a | 19.3 ns |
| Miss Muffet | 15.2 ns | 33.3 ns | 24.0 b | 17.4 ns |
| | **Leaf width (cm)** | | **Quality rating** | |
| Cultivars | Intact | De-eye | Intact | De-eye |
| Hearts Desire | 19.6 a | 13.6 a | 3.0 ns | 4.0 ns |
| Miss Muffet | 15.6 b | 11.2 b | 3.5 ns | 4.5 ns |

[z]Number of days from planting to the first unfurled leaf. Mean separation within column for each cultivar by Fisher's least-significant-difference test at P ≤ 0.05.
ns: not significantly different at P ≤ 0.05.

As shown in Table 5, tubers of this cultivar sprouted quickly after planting, 16 days for intact tubers and 24 days for de-eyed tubers, 2 days earlier than or similar to the sprouting time of 'Miss Muffet'. Plants of 'Hearts Desire' from intact tubers were 51% taller than plants of 'Miss Muffet' (39.6 vs. 26.3 cm), and the leaves of 'Hearts Desire' were 25% longer and 26% wider than the leaves of 'Miss Muffet'. Intact plants of 'Hearts Desire' received a similar quality rating with intact plants of 'Miss Muffet' (3.0 and 3.5). Plants of 'Hearts Desire' grown from de-eyed tubers were 51% taller than those of 'Miss Muffet', but had similar numbers of leaves with the plants of 'Miss Muffet (30.2 and 33.3). Leaves of 'Hearts Desire' plants were similar to those of 'Miss Muffet' in length but 2.4 cm wider. Plants of 'Hearts Desire' forced from de-eyed tubers received a plant quality rating of 4.0, similar to the plant quality rating of 'Miss Muffet' (4.5).

We claim:

1. A new and distinct *Caladium* plant named 'Hearts Desire' as illustrated and described herein.

* * * * *